(12) United States Patent
Schmidt et al.

(10) Patent No.: US 6,242,583 B1
(45) Date of Patent: Jun. 5, 2001

(54) CARBOHYDRATE DERIVATIVES AND THEIR SOLID-PHASE SYNTHESIS

(75) Inventors: Richard R. Schmidt, Constance (DE); Jörg Rademann, Kreuzlingen (CH)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/171,566

(22) PCT Filed: May 9, 1997

(86) PCT No.: PCT/EP97/02393

§ 371 Date: Oct. 21, 1998

§ 102(e) Date: Oct. 21, 1998

(87) PCT Pub. No.: WO97/45436

PCT Pub. Date: Dec. 4, 1997

(30) Foreign Application Priority Data

May 24, 1996  (DE) .............................................. 196 21 177

(51) Int. Cl.⁷ ................ C07H 1/00; C07G 3/00
(52) U.S. Cl. .................. 536/4.1; 536/1.11; 536/18.5; 525/54.2
(58) Field of Search .................... 536/1.11, 4.1, 536/18.5; 525/54.2

(56) References Cited

U.S. PATENT DOCUMENTS

| 5,237,016 | 8/1993 | Ghosh | 525/329 |
|---|---|---|---|
| 5,288,514 | 2/1994 | Ellman | 427/2 |
| 5,399,501 | 3/1995 | Pope | 436/532 |
| 5,412,087 | 5/1995 | McGall | 536/24.3 |

FOREIGN PATENT DOCUMENTS

| 92/00091 | 1/1992 | (WO) . |
|---|---|---|
| 95/03315 | 2/1995 | (WO) . |
| 95/16712 | 6/1995 | (WO) . |
| 95/30642 | 11/1995 | (WO) . |
| 96/00148 | 1/1996 | (WO) . |
| 96/00391 | 1/1996 | (WO) . |

OTHER PUBLICATIONS

Zuckermann et al. Nucleic Acids Research vol. 15, No. 13 pp. 5305–5321, Jul. 1987.*
Rademann et al. Tetrahedron Letters vol. 37, No. 23 pp. 3989–3990, Jul. 1987.*
Xie et al., A Brief, Sterocontrolled Synthesis of C–Vinyl . . ., Dept. of Chem. State Univ. of N.Y.
Sci. vol. 260, May 23, 1993, Danishefsky et al. 1307–09.
J. Am. Chem. Soc., 1994, 116, 1135–1136.
J. Am. Chem. Soc., 1994, 116, 6953–6954.
J. Med. Chem. vol. 37, No. 9, Apr. 29, 1994, 1233–1401.
Int. J. Peptide Protein Res. 41, 1993, 201–203.

* cited by examiner

*Primary Examiner*—Bennett Celsa
(74) *Attorney, Agent, or Firm*—Keil & Weinkauf

(57) ABSTRACT

The invention relates to carbohydrate derivatives, to a process for their preparation and to their use.

4 Claims, No Drawings

CARBOHYDRATE DERIVATIVES AND THEIR SOLID-PHASE SYNTHESIS

This application is a 371 of PCT/EP97/02393, filed May 25, 1996.

The invention relates to carbohydrate derivatives, to a process for their preparation and to their use.

1. Background of the Invention

In classical research to find active substances, the biological effect of novel compounds has been tested in a random screening on the whole organism, for example the plant or the micro-organism. In this case, the limiting factor was the biological testing in constrast to the synthetic chemistry. The provision of molecular test systems by molecular and cell biology has drastically changed the situation.

A large number of molecular test systems such as receptor binding assays, enzyme assays and cell-cell interaction assays has been and is being developed for modern research looking for active substances. Automation and miniaturization of these test systems makes a high sample throughput possible. This development allows an increasing number of chemicals to be tested in ever shorter times for their biological effect in random screening and thus for possible use as lead structure for an active substance in medicine, veterinary medicine or crop protection.

A modern automated test system allows 100,000 or more chemicals to be tested for their biological effect in a mass screening per year.

Classical synthetic chemistry has become, owing to this development, the limiting factor in research looking for active substances.

If the efficiency of these test systems is to be fully exploited, there must be a considerable increase in the efficiency of the chemical synthesis of lead structures for active substances.

Combinatorial chemistry can contribute to this necessary increase in efficiency, in particular when it makes use of automated solid-phase synthetic methods (see, for example, review articles J. Med. Chem. 1994, 37 (1994) 1233 and 1385). Combinatorial chemistry makes it possible to synthesize a wide range of different chemical compounds, called substance libraries. Solid-phase synthesis has the advantage that by-products and excess reactants can easily be removed so that elaborate purification of the products is unnecessary. The finished synthetic products can be passed onto the mass screening directly, ie. bound to the support, or after elimination from the solid phase. Intermediates can also be tested in the mass screening.

2. Description of Prior Art

Applications described to date are mainly restricted to the peptide and nucleotide sectors (Lebl et al., Int. J. Pept. Prot. Res. 41 (1993) 203 and WO 92/00091) or their derivatives (WO 96/00391). Since peptides and nucleotides have only limited use as drugs because of their unfavorable pharmacological properties, it is desirable to utilize the solid-phase synthetic methods which are known and of proven use in peptide and nucleotide chemistry for synthetic organic chemistry.

U.S. Pat. No. 5,288,514 reports one of the first combinatorial solid-phase syntheses in organic chemistry outside peptide and nucleotide chemistry. U.S. Pat. No. 5,288,514 describes sequential synthesis of 1,4-benzodiazepines on a solid phase.

WO 95/16712, WO 95/30642 and WO 96/00148 describe other solid-phase syntheses of potential active substances in combinatorial chemistry.

However, in order to utilize fully the possibilities of modern test systems in mass screening it is necessary continually to feed novel compounds with maximum structural diversity into the mass screening. This procedure makes it possible considerably to reduce the time for identifying and optimizing a novel lead structure of active substances.

It is therefore necessary continually to develop novel different combinatorial solid-phase syntheses. It is sensible for this to be aimed at biologically active compounds.

Carbohydrates and their derivatives are compounds which are in demand in many areas and are difficult to synthesize. Thus, some polysaccharides such as schizophylhan, are used as antitumor agents.

A large number of antibiotics have carbohydrate residues, such as antibiotics from the group of macrolides, anthracyclines or enediynes or consist entirely of carbohydrates, such as streptomycin which is used, for example, in veterinary medicine or in the treatment of plant diseases.

Glycoconjugates such as glycoproteins and/or glycolipids play a crucial part in cell-cell interaction, in the transformation of normal body cells into tumor cells and in inflammatory or allergenic processes in the body. Thus, for example sialyl-Lewis X is a glycoconjugate which has been intensively researched and which is distinguished by its antiunflammatory effect.

Schuster et al. (Abstr. Pap. Am. Chem. Soc., 1994, 207 Meet. Pt. 1, CARB29 and J. Am. Chem. Soc., 1994, 116, 1135–36) describe an enzymatic solid-phase synthesis of a carbohydrate derivative using glycosyltransferases. Schuster et al. use for their synthesis a glycopeptide which has been bound by a linker which can be cleaved by proteases to an aminoprdpyl-silica gel support. This glycopeptide is used as acceptor for glycosyltransferase-catalyzed glycosylation reactions for assembling a sialyl-Lewis X residue. The disadvantages of this method are that glycosyltransferases are sensitive enzymatic catalysts which are not available generally and in the desired amount. It has not been possible to achieve complete conversion of the reactants, so that reaction mixtures were obtained after elimination. Their high specificity, which is advantageous for the individual reaction, results in not every sugar and every position on the various sugars being amenable to enzymatic glycosylation reactions. The linker which can be cleaved by proteases is only provisionally suitable for chemical sugar synthesis, so that a combination of chemical and enzymatic sugar synthesis in order to extend to all sugars and positions on the sugar equally well is impossible with this linker.

Kahn et al. describe, in J. Am. Chem. Soc. 116 (1994) 6953 et seq. a carbohydrate synthesis on a thiophenol-resin. The disadvantage of this method is that to eliminate the glycoside it is necessary to use mercury trifluoroacetate which is toxic and difficult to remove. This makes further purification of the synthetic products necessary. The elimination of the glycoside from the support additionally results only in the free sugars without it being possible to form a new linkage at the cleaved bond and thus introduce a new substituent.

The glycosylation reaction can be carried out in this method only with highly reactive sulfoxides at low temperatures, and very stable protective groups are additionally necessary.

The solid-phase synthesis described by Danishefsky et al. (Science, 260 (1993) 1307 et seq. and 269 (1995) 202 et seq.) for glycosides are [sic] restricted to glycals as precursors, ie. as donors. In addition, only 1–6 glycosidic linkages can be formed and, as in the case of Kahn et al., no other new substituent can be introduced on elimination from the support.

SUMMARY OF THE INVENTION

It is an object of the present invention to provide a rapid and efficient solid-phase process for preparing carbohydrate derivatives which does not have the abovementioned disadvantages and meets the requirements of combinatorial chemistry.

DETAILED DESCRIPTION OF THE INVENTION

We have found that this object is achieved by a process for preparing carbohydrate derivatives of the formula I

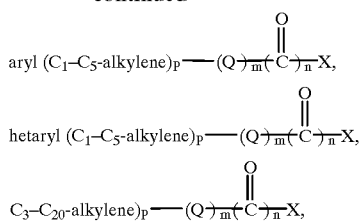
(I)

in which the variables and substituents have the following meanings:

(P) a solid phase
(L) an aliphatic linker having 2 to 12 carbon atoms,
$R^1$ $CHR^5R^6$, $R^5$
$R^2$, $R^3$, $R^4$ independently of one another hydrogen, XH, substituted or unsubstituted

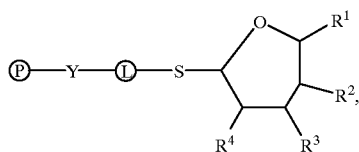

$C_1$–$C_{20}$alkyl——$(Q)_m(C)_nX$, $C_3$–$C_{10}$cycloalkyl——$(Q)_m(C)_nX$, aryl ($C_1$–$C_5$-alkylene)$_p$——$(Q)_m(C)_nX$, hetaryl ($C_1$–$C_5$-alkylene)$_p$——$(Q)_m(C)_nX$, $C_3$–$C_{20}$-alkylene)$_p$——$(Q)_m(C)_nX$, ($C_1$–$C_4$-alkyl )$_3$SiO, diaryl ($C_1$–$C_5$-alkyl )SiO, aryl ($C_1$–$C_5$-dialkyl)SiO or $R^7$ and m=0, 1; n=0, 1; p=0, 1 or two adjacent radicals $R^2$, $R^3$, $R^4$, $R^6$ independently of one another form a substituted or unsubstituted arylalkylidene acetal or an alkylidene acetal,
$R^5$ hydrogen, substituted or unsubstituted $C_1$–$C_{20}$-alkyl, $C_3$–$C_{20}$ alkenyl, arylalkylene arylalkyl or aryl,
$R^6$ hydrogen, XH, substituted or unsubstituted

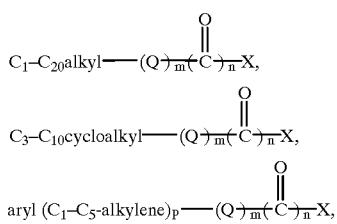

$C_1$–$C_{20}$alkyl——$(Q)_m(C)_nX$, $C_3$–$C_{10}$cycloalkyl——$(Q)_m(C)_nX$,

-continued aryl ($C_1$–$C_5$-alkylene)$_p$——$(Q)_m(C)_nX$, hetaryl ($C_1$–$C_5$-alkylene)$_p$——$(Q)_m(C)_nX$, $C_3$–$C_{20}$-alkylene)$_p$——$(Q)_m(C)_nX$, ($C_1$–$C_4$-alkyl)$_3$SiO, diaryl($C_1$–$C_5$-alkyl)SiO, aryl ($C_1$–$C_5$-dialkyl)SiO or $R^7$ and m=0, 1; n=0, 1; p=0, 1 or (aryl)$_3$CO,
$R^7$ is a group [sic] of the formula IV

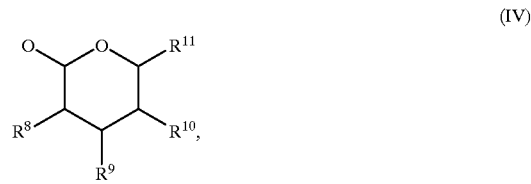
(IV)

where the substituents $R^8$, $R^9$, $R^{10}$, $R^{11}$ have the following meanings:
$R^8$, $R^9$, $R^{10}$ independently of one another have the meanings described for the radicals $R^2$, $R^3$, $R^4$ and may be identical to or different from the radicals $R^2$, $R^3$, $R^4$,
$R^{11}$ $CHR^5R^6$, $R^5$ or two adjacent radicals $R^8$, $R^9$, $R^{10}$, $R^6$ independently of one another may form a substituted or unsubstituted aryl-alkylidene acetal or an alkylidene acetal,
Q O, NH
O, NR$^{12}$
Y O, S
$R^{12}$ hydrogen, substituted or unsubstituted $C_1$–$C_{10}$alkyl, $C_3$–$C_8$-cycloalkyl, aryl, hetaryl, arylalkyl
which comprises coupling compounds of the formula II

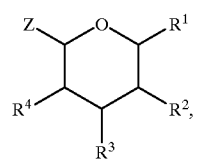
(II)

where Z is selected from the group N$^3$, halogen,

OCH$_2$CH$_2$CH$_2$CH=CH$_2$, OPO$_2$H$_2$, S-aryl, S-alkyl
in the presence of a promotor to a functionalized solid phase of the formula III

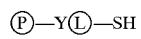 (III).

The invention additionally relates to novel carbohydrate derivatives and to their use.

It is possible to use as solid phase (P) in the process according to the invention supports known from solid-phase peptide synthesis. Usable supports can consist of a large number of materials as long as they are compatible with the synthetic chemistry used. The size of the supports can be varied within wide limits depending on the material. Particles in the range from 1 μm to 1.5 cm are preferably used as supports, particularly preferably particles in the range from 1 μm to 150 μm in the case of polymeric supports.

The shape of the supports is not critical, but spherical particles are preferred. The supports may have a homogeneous or heterogeneous size distribution, but homogeneous particle sizes are preferred.

Examples of suitable solid phases (P) are ceramics, glass, latex, functionalized crosslinked polystyrenes, polyacrylamides, silica gels or resins.

In order to allow attachment of the reactant and elimination of the synthetic product after the synthesis, the support must be suitably functionalized or provided with a linker which has an appropriate functional group. Suitable and preferred supports and support-linker conjugates are, or example, chlorobenzyl-resin (Merrifield resin), Rink resin (Novabiochem), Sieber resin (Novabiochem), Wang resin (Bachem), Tentagel resins (Rapp-Polymere), Pega resin (Polymer Laboratories) or polyacrylamides. Chlorobenzyl-resin is particularly preferred as support.

For attachment of the preferred aliphatic linker (formula VI)

HY—(L)—SH  (VI)

having 2 to 12 carbon atoms, where Y is oxygen or sulfur, to the solid phase, the latter must be modified where appropriate in a manner known to the skilled worker.

For example, solid phases based on polyacrylamides can be derivatized with 4-chloromethylbenzoic acid in such a way that the linker (=formula VI) can be attached to the solid phase, and the latter can thus be functionalized in a suitable manner for the synthesis (scheme I).

Scheme I:

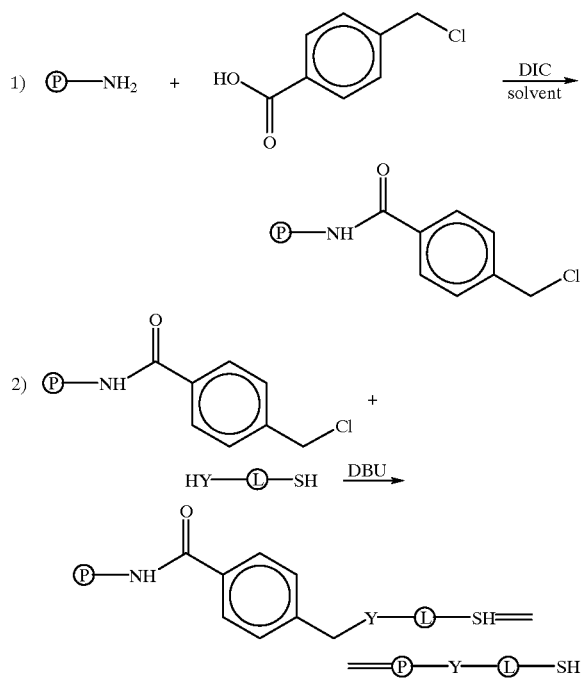

The amide linkage (1) between the support and the 4-chloromethylbenzoic acid can be formed in a solvent with the aid of, for example, diisopropylcarbodiimide (=DIC). Other coupling reagents suitable for forming the amide linkage are, for example, TBTU, HBTU, BOP or PYBOP (Lit.: Int. J. Peptide Prot. Rev. [sic] 35 (1990) 161–214). If Y is oxygen, the sulfur present in the linker is provided with a protective group, eg. trityl. This technique can also be used in the case where Y is sulfur. The coupling of the preferred linker with Y=S to the support can, however, also take place directly without a protective group.

Suitable solvents for forming the functionalized solid phase are aprotic, nonpolar or polar solvents, for example DMF, $CH_2Cl_2$, DMSO or THF. It is possible to use single solvents or mixtures.

To determine the concentration of thiol groups in the solid phase provided with the linker, elemental analysis was used to determine the percentage content of various elements such as C, H, S etc. The S content of the solid phase is a measure of the free thiol groups on the support. The thiol group concentration is in the range from 0.05 to 0.9 mmol/g of resin, preferably from 0.2 to 0.6 mmol/g of resin.

The linker (=L) can be branched or unbranched, chiral or achiral.

Examples of dithiols which may be mentioned are 1,3-propanedithiol, 1,2-propanedithiol, 1,2-butanedithiol, 1,3-butanedithiol, 1,4-butanedithiol, 2,3-butanedithiol, 1,2-pentanedithiol, 1,3-pentanedithiol, 1,4-pentanedithiol, 1,5-pentanedithiol, 2,4-pentanedithiol, 2-methyl-1,4-butanedithiol, 1,2-hexanedithiol, 1,3-hexanedithiol, 1,4-hexanedithiol, 1,5-hexanedithiol, 1,6-hexanedithiol, 2,3-hexanedithiol, 2,4-hexanedithiol, 2,5-hexanedithiol, 2-methyl-1,5-pentanedithiol, 1,5-dithiomethylcyclohexane or 3-methyl-1,5-pentanedithiol.

Reaction (2) is carried out at from 30 to 100° C., preferably 20 to 50° C.

The synthetic product I can be eliminated from the solid functionalized phase in the presence of at least one thiophilic reagent and of at least one alcohol.

Examples of suitable thiophilic reagents are dimethyl(methylthio)sulfonium triflate (=DMTST) or the corresponding dimethyl(methylthio) tetrafluoroborate (=DMTSB). Other suitable reagents are described, for example, by Waldmann H. in Nachr. Chem. Tech. Lab. 39 (1991) 675–682. The synthetic product I can moreover easily be eliminated from the linker of the functionalized solid phase using bromonium ions in solvent/water mixtures, preferably acetone/water, particularly preferably acetone/water (9:1), in which case the free sugars are obtained. Alcohols suitable in principle are all alcohols such as primary or secondary alcohols, monohydric or polyhydric alcohols. Examples which may be mentioned here are branched or unbranched, saturated or mono- or polyunsaturated $C_1$–$C_{20}$ alcohols such as methanol, ethanol, 1-propanol, 2-propanol, 1-butanol, 2-butanol, 2-methyl-1-propanol, 1-pentanol, 2-pentanol, 3-pentanol, 2-methyl-1-butanol, 3-methyl-1-butanol, 2-methyl-3-butanol, 3-methyl-2-butanol, hexanol, heptanol, octanol, nonanol, decanol, undecanol, dodecanol, tridecanol, tetradecanol, pentadecanol, hexadecanol, heptadecanol, octadecanol, nonadecanol, eicosanol or fatty alcohols derived from fatty acids such as palmitic acid, palmitoleic acid, stearic acid, oleic acid, eicosatrienoic acid, linoleic acid, linolenic acid, arachidonic acid. Mention may furthermore be made by way of example of alcohols from terpenoid metabolism, such as menthol, geraniol, farnesol or polyhydric alcohols such as glycol, glycerol, pentitols such as adonitol, arabitol or xylitol, hexitols such as sorbitol, dulcitol or mannitol.

Likewise suitable are hydroxy carboxylic acids such as lactic acid, mandelic acid, pantoic acid, 3-phenyllactic acid, 2-hydroxybutyric acid, 3-hydroxybutyric acid, 4-hydroxybutyric acid, β-hydroxyisobutyric acid, tartaric acid, citric acid, or the various hydroxy fatty acids in the form of their esters or steroids such as cholic acid, deoxycholic acid in the form of their esters, corticosterone, aldosterone, estrone, estradiol, testosterone or ecdysone.

Also suitable as polyols for the elimination of sugars such as glucose, galactose, mannose, fucose, xylose, arabinose, altrose, allose, rhamnose, gulose, idose, talose, fructose, sorbose, tagatose, ribose, deoxyribose, aminosaccharides such as N-acetylneuraminsic acid, N-acetyl-D-glucosamine, N-acetyl-D-galactosamine, N(α-D-glucopyranosyl) methylamine, D-glucosamine, (2-amino-2-deoxy-D-glucose), N-acetylmuramic acid, D-galactos-amine(2-amino-2-deoxy-D-galactose) or disaccharides such as maltose, lactose, chitobiose, cellobiose or oligosaccharides, in all their stereoisomeric forms (a or configuration) and all their possible linkage types [α-(1,3)-,α-(1,4)-,α-(1,6)-,β-(1,2)-,β-(1,3)-,β-(1,4)-β-(1,6)-] in the case of oligosaccharides.

$R^1$ in the compounds of the formulae I, II and V is $CHR^5R^6$ and $R^5$.

For $R^5$, mention may be made of hydrogen, substituted or unsubstituted $C_1$–$C_{20}$-alkyl, $C_3$–$C_{20}$-alkenyl, arylalkyl or aryl.

Alkyl radicals which may be mentioned are branched or unbranched $C_1$–$C_{20}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-l-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl. Suitable substituents are one or more substituents such as halogen such as fluorine, chlorine or bromine, cyano, nitro, amino, hydroxyl, alkyl, aryl, alkoxy, carboxyl, benzyloxy, phenyl or benzyl.

Alkenyl radicals which may be mentioned are branched or unbranched $C_3$–$C_{20}$-alkenyl chains such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl, decenyl, undecenyl, dodecenyl, tridecenyl, tetradecenyl, pentadecenyl, hexadecenyl, heptadecenyl, octadecenyl, nonadecenyl or eicosenyl.

Suitable substituents are one or more substituents such as halogen such as fluorine, chlorine or bromine, cyano, nitro, amino, hydroxyl, alkyl, aryl, alkoxy, carboxyl, benzyloxy, phenyl or benzyl.

Arylalkyl radicals which may be mentioned are phenyl-($C_1$–$C_5$-alkylene) or naphthyl-($C_1$–$C_5$-alkylene) radicals which have branched or unbranched chains, such as phenylmethyl, phenylethyl, phenypropyl, phenyl-1-methylethyl, phenylbutyl, phenyl-1-methylpropyl, phenyl-2-methylpropyl, phenyl-1,1-dimethylethyl, phenyl-2-methylpropyl, phenyl-1,1-dimethylethyl, phenylpentyl, phenyl-1-methylbutyl, phenyl-20-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-2-methylpropyl, naphthyl-1,1-dimethylethyl, naphthylpentyl, naphthyl-1-methylbutylene [sic], naphthyl-2-methylbutyl, dimethylpropyl, or naphthyl-1-ethylpropyl, and their isomeric or stereoisomeric forms. Aryl radicals which may be mentioned are substituted or unsubstituted phenyl or naphthyl radicals.

The arylalkyl radicals or aryl radicals may, where appropriate, be substituted by one or more radicals such as halogen such as fluorine, chlorine or bromine, cyano, nitro, amino, hydroxyl, alkyl, alkoxy or other radicals.

For $R^6$, mention may be made of hydrogen, XH, substituted or unsubstituted

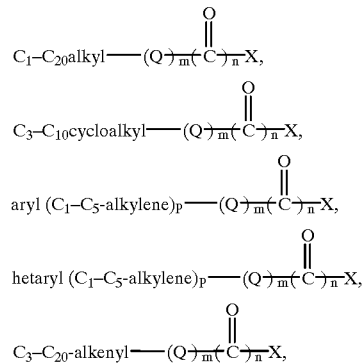

$(C_1$–$C_4alkyl)_3SiO$, $diaryl(C_1$–$C_5alkyl)SiO$, $Aryl(C_1$–$C_5$-dialkyl)SiO$ or $R^7$, where Q is oxygen or NH, X is oxygen or $NR^{12}$, m, n and p are, independently of one another, 0 or 1.

Alkyl radicals in the formula

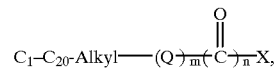

which may be mentioned are branched or unbranched $C_1$–$C_{20}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Cycloalkyl radicals in the formula

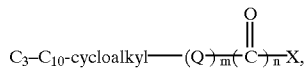

which may be mentioned are branched or unbranched $C_3$–$C_{10}$-cycloalkyl having 3 to 7 carbon atoms in the ring or ring system, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

The cycloalkyl radicals may, where appropriate, be substituted by one or more radicals such as halogen such as fluorine, chlorine or bromine, cyano, nitro, amino, hydroxyl, alkyl, alkoxy or other radicals, or contain heteroatoms such as S, N and O in the ring.

Arylalkyl radicals in the formula

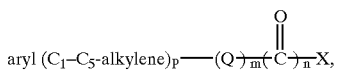

which may be mentioned are phenyl-($C_1$–$C_5$-alkylene) or naphthyl-($C_1$–$C_5$-alkylene) radicals which have branched or unbranched chains, such as phenylmethyl, phenylethyl, phenylpropyl, phenyl-1-methylethyl, phenylbutyl, phenyl-1-methylpropyl, phenyl-2-methylpropyl, phenyl-1,1-dimethylethyl, phenylpentyl, phenyl-1-methylbutyl, phenyl-2-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-=2-methylpropyl, naphthyl-1,1-dimethylethyl, naphthylpentyl, naphthyl-1-methylbutyl, naphthyl-2-methylbutyl, naphthyl-3-methylbutyl, naphthyl-2,2-dimethylpropyl, or naphthyl-1-ethylpropyl, and their isomeric or stereoisomeric forms.

Aryl means, for example, phenyl, methoxyphenyl or naphthyl, or aromatic rings or ring systems having 6 to 18 carbon atoms in the ring system, and up to 24 other carbon atoms which may form other nonaromatic rings or ring systems having 3 to 8 carbon atoms in the ring, which may, where appropriate, be substituted by one or more radicals such as halogen such as fluorine, chlorine or bromine, cyano, nitro, amino, hydroxyl, alkyl, alkoxy or other radicals. Unsubstituted or substituted phenyl, methoxyphenyl and naphthyl are preferred.

Hetaryl(alkylene) radicals in the formula

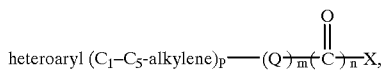

mean hetaryl radicals which contain single or fused aromatic ring systems having one or more heteroaromatic 5- to 7-membered rings which contain one or more nitrogen, sulfur and/or oxygen atoms, and which are connected where appropriate to a branched or unbranched $C_1$–$C_5$-alkylene chain such as methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene or 1-ethylpropylene.

Alkenyl radicals in the formula

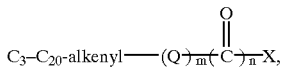

which may be mentioned are branched or unbranched $C_3$–$C_{20}$-alkenyl chains such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl; 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl, decenyl, undecenyl, dodecenyl, tridecenyl, tetradecenyl, pentadecenyl, hexadecenyl, heptadecenyl, octadecenyl, nonadecenyl or eicosenyl.

Suitable substituents for the various radicals $R^6$ mentioned are one or more substituents such as halogen such as fluorine, chlorine or bromine, cyano, nitro, amino, hydroxyl, alkyl, aryl, alkoxy, carboxyl or benzyloxy.

Alkyl radicals in the radical ($C_1$–$C_4$-alkyl)$_3$SiO which may be mentioned are branched or unbranched alkyl chains such as methyl, ethyl, n-propyl, 1-methylethyl, n-butyl, 1-methylpropyl, 2-methylpropyl or 1,1-dimethylethyl.

Diaryl in the formula diaryl($C_1$–$C_5$-alkyl)SiO means, for example, diphenyl, dinaphthyl or phenylnaphthyl, with $C_1$–$C_5$-alkyl being branched or unbranched alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl or 1-ethylpropyl.

Aryl radicals in the radical aryl($C_1$–$C_5$-dialkyl)SiO which may be mentioned are, for example, phenyl, methoxyphenyl or naphthyl, with $C_1$–$C_5$-dialkyl being branched or unbranched alkyl chains which may be identical or different, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl or 1-ethylpropyl.

$R^7$ is a compound of the formula IV

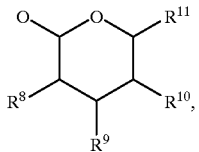

where the substituents $R^8$, $R^9$, $R^{10}$, $R^{11}$ have the following meanings:

$R^{11}$ is $CHR^5R^6$ and $R^5$, $R^8$, $R^9$, $R^{10}$ have, independently of one another, the meanings described below for the radicals $R^2$, $R^3$, $R^4$ and can be identical to or different from the radicals $R^2$, $R^3$, $R^4$ or two adjacent radicals $R^8$, $R^9$, $R^{10}$, $R^6$ can form, independently of one another, a substituted or unsubstituted arylalkylidene acetal or an alkylidene acetal.

Suitable substituents are one or more substituents such as halogen such as fluorine, chlorine or bromine, cyano, nitro, amino, hydroxyl, alkyl, aryl, alkoxy, carboxyl or benzyloxy.

$R^{12}$ which may be mentioned is hydrogen, substituted or unsubstituted $C_1$–$C_{10}$-alkyl, $C_3$–$C_8$-cycloalkyl, aryl, hetaryl or arylalkyl, where alkyl is branched or unbranched $C_1$–$C_{10}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl or n-octyl, n-nonyl or n-decyl;

cycloalkyl is branched or unbranched $C_3$–$C_8$-cycloalkyl having 3 to 7 carbon atoms in the ring, which may contain heteroatoms such as S, N or O , such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl [sic], 1,2-dimethylcyclopropyl, 1-methyl-2-ethylcyclopropyl or cyclooctyl;

aryl is phenyl or naphthyl;

hetaryl is a single or fused aromatic ring system having one or more heteroaromatic 3- to 7-membered rings, arylalkyl is a phenyl-($C_1$–$C_5$-alkyl) or naphthyl-($C_1$–$C_5$-alkyl) radical which has branched or unbranched chains, such as phenylmethyl, phenylethyl, phenylpropyl, phenyl-1-methylethyl, phenylbutyl, phenyl-1-methylpropyl, phenyl-2-methylpropyl, phenyl-1,1-dimethylethyl, phenylpentyl, phenyl-1-methylbutyl, phenyl-2-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-2-methylpropyl, naphthyl-1,1-dimethylethyl, naphthylpentyl, naphthyl-1-methylbutyl, naphthyl-2-methylbutyl, naphthyl-3-methylbutyl, naphthyl-2,2-dimethylpropyl, or naphthyl-1-ethylpropyl, and their isomeric or stereoisomeric forms.

All the $R^{12}$ radicals mentioned can be unsubstituted or substituted by at least one other radical from the group of halogen such as fluorine, chlorine or bromine, cyano, nitro, amino, hydroxyl or other radicals.

A radical which may also be mentioned for $R^6$ is (aryl)$_3$CO where aryl is phenyl or naphthyl which may be unsubstituted or substituted by at least one other radical such as halogen such as fluorine, chlorine or bromine, cyano, nitro, amino, hydroxyl, alkyl, aryl, alkoxy, carboxyl or benzyloxy.

Radicals which may be mentioned for $R^2$, $R^3$ and $R^4$ in the compounds of the formulae I, II or V are, independently of one another, hydrogen, XH, substituted or unsubstituted

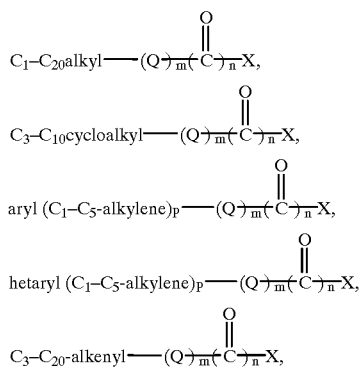

($C_1$–$C_4$alkyl)$_3$SiO, diaryl($C_1$–$C_5$alkyl)SiO, Aryl($C_1$–$C_5$-dialkyl)SiO or $R^7$, where Q is oxygen or NH, X is oxygen or $NR^{12}$, m, n and p are, independently of one another, 0 or 1.

Alkyl radicals in the formla

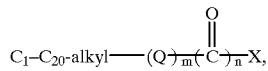

which may be mentioned are branched or unbranched $C_1$–$C_{20}$-alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Cycloalkyl radicals in the formula

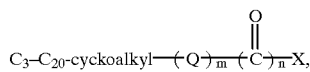

which may be mentioned are branched or unbranched $C_3$–$C_{10}$-cycloalkyl having 3 to 7 carbon atoms in the ring or ring system, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl [sic], 1,2-dimethylcyclypropyl [sic], 1-methyl-2-ethylcyclopropyl, cyclooctyl, cyclononyl or cyclodecyl.

The cycloalkyl radicals may, where appropriate, be substituted by one or more radicals such as halogen such as fluorine, chlorine or bromine, cyano, nitro, amino, hydroxyl, alkyl, alkoxy or other radicals, or contain heteroatoms such as S, N or O in the ring.

Arylalkyl radicals in the formula

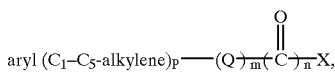

which may be mentioned are phenyl-($C_1$–$C_5$-alkylene) or naphthyl-($C_1$–$C_5$-alkylene) radicals which have branched or unbranched chains, such as phenylmethyl, phenylethyl, phenylpropyl, phenyl-1-methylethyl, phenylbutyl, phenyl-1-methylpropyl, phenyl-2-methylpropyl, phenyl-1,1-dimethylethyl, phenylpentyl, phenyl-1-methylbutyl, phenyl-2-methylbutyl, phenyl-3-methylbutyl, phenyl-2,2-dimethylpropyl, phenyl-1-ethylpropyl, naphthylmethyl, naphthylethyl, naphthylpropyl, naphthyl-1-methylethyl, naphthylbutyl, naphthyl-1-methylpropyl, naphthyl-=2-methylpropyl, naphthyl-1,1-dimethylethyl, naphthylpentyl, naphthyl-1-methylbutyl, naphthyl-2-methylbutyl, naphthyl-3-methylbutyl, naphthyl-2,2-dimethylpropyl, or naphthyl-1-ethylpropyl, and their isomeric or stereoisomeric forms.

Aryl means, for example, phenyl, methoxyphenyl or naphthyl, or aromatic rings or ring systems having 6 to 18 carbon atoms in the ring system, and up to 24 other carbon atoms which may form other nonaromatic rings or ring systems having 3 to 8 carbon atoms in the ring, which may, where appropriate, be substituted by one or more radicals such as halogen such as fluorine, chlorine or bromine, cyano, nitro, amino, hydroxyl, alkyl, alkoxy or other radicals. Unsubstituted or substituted phenyl, methoxyphenyl and naphthyl are preferred.

Heteroarylalkyl radicals in the formula

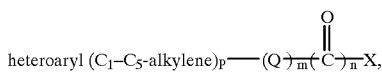

mean hetaryl radicals which contain single or fused aromatic ring systems having one or more heteroaromatic 5- to 7-membered rings which contain one or more nitrogen, sulfur and/or oxygen atoms, and which are connected where appropriate to a branched or unbranched $C_1$–$C_5$-alkyl chain such as methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene or 1-ethylpropylene.

Alkenyl radicals in the formula

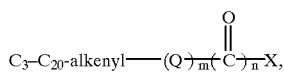

which may be mentioned are branched or unbranched $C_3$–$C_{20}$-alkenyl chains such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl, decenyl, undecenyl, dodecenyl, tridecenyl, tetradecenyl, pentadecenyl, hexadecenyl, heptadecenyl, octadecenyl, nonadecenyl or eicosenyl.

Suitable substituents for the various $R^2$, $R^3$ and $R^4$ radicals mentioned are one or more substituents such as halogen such as fluorine, chlorine or bromine, cyano, nitro, amino, hydroxyl, alkyl, aryl, alkoxy, carboxyl or benzyloxy.

Alkyl radicals in the radical ($C_1$–$C_4$-alkyl)$_3$SiO which may be mentioned are branched or unbranched alkyl chains such as methyl, ethyl, n-propyl, 1-methylethyl, n-butyl, 1-methylpropyl, 2-methylpropyl or 1,1-dimethylethyl.

Diaryl in the formula diaryl($C_1$–$C_5$-alkyl)SiO means, for example, diphenyl, dinaphthyl or phenylnaphthyl, with $C_1$–$C_5$-alkyl being branched or unbranched alkyl chains such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl or 1-ethylpropyl.

Aryl radicals in the radical aryl($C_1$–$C_5$-dialkyl)SiO which may be mentioned are, for example, phenyl, methoxyphenyl or naphthyl, with $C_1$–$C_5$-dialkyl being branched or unbranched alkyl chains which may be identical or different, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl or 1-ethylpropyl.

$R^7$ is a compound [sic] of the formula IV

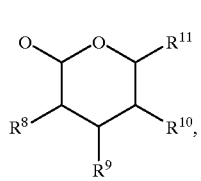

(IV)

where the substituents $R^8$, $R^9$, $R^{10}$, $R^{11}$ and $R^{12}$ have the meanings described above.

For $R^{13}$ in the formula V mention may be made of substituted or unsubstituted $C_1$–$C_{20}$-alkyl, $C_3$–$C_{20}$-alkenyl, $C_1$–$C_5$-alkylhetaryl, $C_3$–$C_{10}$-cycloalkyl or substituted or unsubstituted $C_5$–$C_{25}$-cycloalkyl which is bridged once to four times and may be substituted by at least substituent selected from the group of $C_1$–$C_{10}$-alkyl, $C_3$–$C_{10}$-alkenyl, CO, COO-($C_1$–$C_{10}$-alkyl), OH, O-($C_1$–$C_{10}$-alkyl), O-alkylhetaryl or O-alkylaryl, or substituted or unsubstituted mono-, di- or oligosaccharides or hydroxy carboxylic acids, where the radicals and substituents have the following meanings:

alkyl is branched or unbranched $C_1$–$C_{20}$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosenyl [sic].

Alkenyl is branched or unbranced $C_3$–$C_{20}$-alkenyl such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1, 2-dimethyl-2-propenyl, 1- ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, nonenyl, decenyl, undecenyl, dodecenyl, tridecenyl, tetradecenyl, pentadecenyl, hexadecenyl, heptadecenyl, octadecenyl, nonadecenyl or eicosenyl.

Alkylhetaryl is $C_1$–$C_5$-alkylhetaryl which has branched or unbranched chains and which contains one or more nitrogen, sulfur and/or oxygen atoms in the ring or ring system, cycloalkyl is branched or unbranched $C_3$–$C_{10}$-cycloalkyl having 3 to 7 carbon atoms in the ring, which may contain heteroatoms such as S, N or O, or ring system such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl or cycloalkyl is substituted or unsubstituted branched or unbranched $C_5$–$C_{25}$-cycloalkyl which can be bridged one to four times and can be substituted by at least one substituent selected from the group of $C_1$–$C_{10}$-alkyl, $C_3$–$C_{10}$-alkenyl, CO, COO-($C_1$–$C_{10}$-alkyl), OH, O-($C_1$–$C_{10}$-alkyl), O-alkylhetaryl or O-alkylaryl, where the preferred meanings of said substituents on $C_5$–$C_{25}$-alkyl are alkyl branched or unbranched $C_1$–$C_{10}$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl, alkenyl branched or unbranched $C_3$–$C_8$-alkenyl such as propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl alkylhetaryl $C_1$–$C_5$-alkylhetaryl which has branched or unbranched chains and contains one or more nitrogen, sulfur and/or oxygen atoms in the ring or ring system, alkylaryl $C_1$–$C_6$-alkylphenyl or $C_1$–$C_6$-alkylnaphthyl which has branched or unbranched chains, such as methylphenyl, ethylphenyl, propylphenyl, 1-methylethylphenyl, butylphenyl, 1-methylpropylphenyl, 2-methylpropylphenyl, 1,1- dimethylethylphenyl, pentylphenyl, 1-methylbutylphenyl, 2-methylbutylphenyl, 3-methylbutylphenyl, 2,2-dimethylpropylphenyl, 1-ethylpropylphenyl, n-hexylphenyl, 1,1-dimethylpropylphenyl, 1,2-dimethylpropylphenyl, 1-methylpentylphenyl, 2-methylpentylphenyl, 3-methylpentylphenyl, 4-methylpentylphenyl, 1,1-dimethylbutylphenyl, 1,2-dimethylbutylphenyl, 1,3-dimethylbutylphenyl, 2,2-dimethylbutylphenyl, 2,3-dimethylbutylphenyl, 3,3-dimethylbutylphenyl, 1-ethylbutylphenyl, 2-ethylbutylphenyl, 1,1,2-trimethylpropylphenyl, 1,2,2-trimethylpropylphenyl, 1-ethyl-1-methylpropylphenyl, 1-ethyl-2-methylpropylphenyl, methylnaphthyl, ethylnaphthyl, propynaphthyl [sic], 1-methylethylnaphthyl, butylnaphthyl, 1-methylpropylnaphthyl, 2-methylpropylnaphthyl, 1,1-dimethylethylnaphthyl, pentylnaphthyl, 1-methylbutylnaphthyl, 2-methylbutylnaphthyl, 3-methylbutylnaphthyl, 2,2-dimethylpropylnaphthyl, 1-ethylpropylnaphthyl, n-hexylnaphthyl, 1,1-dimethylpropylnaphthyl, 1,2-dimethylpropylnaphthyl, 1-methylpentylnaphthyl, 2-methylpentylnaphthyl, 3-methylpentylnaphthyl, 4-methylpentylnaphthyl, 1,1-dimethylbutylnaphthyl, 1,2-dimethylbutylnaphthyl, 1,3-dimethylbutylnaphthyl, 2,2-dimethylbutylnaphthyl, 2,3-dimethylbutylnaphthyl, 3,3-dimethylbutylnaphthyl, 1-ethylbutylnaphthyl, 2-ethylbutylnaphthyl, 1,1,2-trimethylpropylnaphthyl, 1,2,2-trimethylpropylnaphthyl, 1-ethyl-1-methylpropylnaphthyl, 1-ethyl-2-methylpropylnaphthyl.

$C_5$–$C_{25}$-Cycloalkyl preferably means steroids such as cholic acid, deoxycholic acid in the form of its esters, corticosterone, aldosterone, estrone, estradiol, testosterone or ecdysone.

Mono-, di- or oligosaccharides such as glucose, galactose, mannose, fucose, xylose, arabinose, altrose, allose, rhamnose, gulose, idose, talose, fructose, sorbose, tagatose, ribose, deoxyribose or aminosaccharids such as N-acetylneuraminic acid, N-acetyl-D-glucosamine, N-acetyl-D-galatosamine [sic], N(α-D-glucopyranosyl)-methylamine, D-glucosamine(2-amino-2-deoxy-D-glucose), N-acetylmuramic acid, D-galactosamine(2-amino-2-deoxy-D-galactose) or disaccharides such as maltose, lactose, chitobiose, cellobiose or oligosaccharides in all their stereoisomeric forms (α or β configurations) and all their possible linkage types [α-(1,3)-, α-(1,4)-, α-(1,6)-, β-(1,2)-, β-(1,3)-, β-(1,4)-, β-(1,6)] as [sic] homo- or heteromers in the case of oligosaccharides can be glycosidically linked.

Hydroxy carboxylic acids such as lactic acid, mandelic acid, pantoic acid, 3-phenyllactic acid, 2-hydroxybutyric acid, 3-hydroxybutyric acid, 4-hydroxybutyric acid, β-hydroxyisobutyric acid, tartaric acid, citric acid, serine, threonine or the various hydroxy fatty acids in the form of their esters.

All said radicals and substituents must, where necessary, be provided with protective groups for the synthesis.

The process according to the invention for preparing the carbohydrate derivatives is advantageously carried out in a reaction sequence in which firstly the solid phase is functionalized suitably with the preferred linker of the formula VI HY——SH  (VI)

The functionalization of chloromethylpolystyrene [=Merrifield resin=(1)] which has been crosslinked with 1% divinylbenzene is carried out as follows, for example:
1st reaction

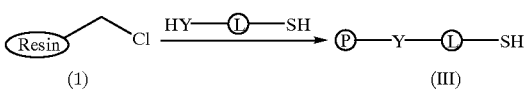

Reaction (1) is carried out in the presence of a base, preferably tertiary amine bases such as (iPr)$_2$NEt, NEt$_3$ or DBU. Other suitable bases are potassium or sodium carbonate or sodium hydride or sodium hexamethyldisilane, and DBU or sodium hydride is preferred. Solvents which may be mentioned are any aprotic solvents, for example DMF, THF, CH$_2$Cl$_2$ or mixtures thereof. The reaction is carried out at a temperature in the range from +10 to 70° C., preferably +10 to +40° C.

Subsequently, in the presence of a promoter, a first sugar which has been activated via a suitable group Z such as N$^3$, halogen,

OCH$_2$CH$_2$CH$_2$CH=CH$_2$, OPO$_2$H$_2$, S-Aryl, S-Alkyl is coupled onto the functionalized solid phase (2nd reaction).
2nd reaction

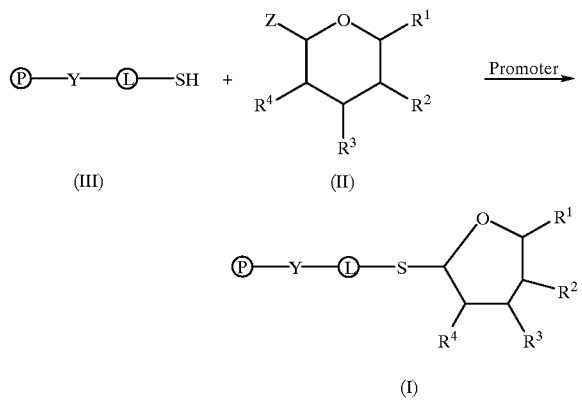

Examples of suitable promoters are Lewis acids such as BF$_3$.Et$_2$O, TMSOTf, TESOTf or electrophilic reagents such as I$_2$, ICl, IBr or thiophilic reagents such as DMTST or heavy metal salts which form halogen salts of low solubility, such as AgOTf, Hg(Cn)$_2$ [sic] or Hg(OTfa)$_2$, with Lewis acids being preferred. Other suitable promoters and suitable glycosyl donors with the various possible leaving groups Z are to be found in Waldmann H. (Nachr. Chem. Tech. Lab. 39, 1991:675–682), Sinaÿ P. (Pure Appl. Chem. 63, 1991:519–528) or Schmidt R. R. (Angew. Chem. 98, 1986: 213–236). The reaction is carried out at from −100° C. to +100° C., preferably from −60° C. to +80° C., very particularly preferably from −20° C. to +40° C. Suitable solvents are any aprotic organic solvents free of hydroxyl groups, such as CH$_2$Cl$_2$, toluene, acetonitrile or mixtures thereof; possibly with the addition of dehydrating reagents such as molecular sieves.

The thioglycoside produced by the attachment of the first sugar to the solid phase can be further modified or converted in various ways as described below.

The protective groups on the various hydroxyl or hydroxymethyl groups of the sugar can be completely or partly eliminated, and the thioglycoside provided with at least one free hydroxyl or hydroxymethyl group can be reacted with the radicals mentioned for $R^1$ to $R^4$ or $R^8$ to $R^{11}$ or with compounds of the formula II. It is possible in this case for identical or different radicals or identical or different compounds of the formula II to be reacted with the hydroxyl or hydroxymethyl groups, with different radicals or compounds of the formula II possibly being reacted sequentially with the carbohydrate, or else mixtures of the components. The reaction in this case preferably takes place with acylating, carbamoylating or alkylating reagents. The free hydroxyl or hydroxymethyl groups can be reacted with more than, equal to or less than one molar equivalent of the radicals or of the compounds of the formula II so that complete or partial conversion of the thioglycoside is achieved. The carbohydrate can subsequently be eliminated from the solid phase with introduction of another substituent, or else be eliminated without introduction of another substituent so that a free hydroxyl group is produced.

In the case where the thioglycoside has been reacted with at least one other carbohydrate, another cycle can be carried out with the variations described above as possibility. Carrying out the synthetic cycle several times allows complex carbohydrates to be assembled.

The synthetic cycle is preferably carried out by deprotecting the radical $R^1$ or, if the synthesis is advanced, the radical $R^{11}$ and thus on the free hydroxymethyl group (reaction 3).

3rd reaction

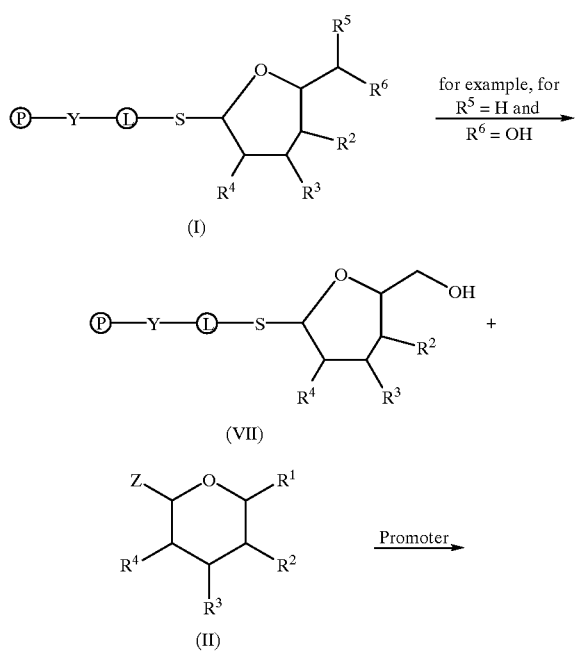

-continued

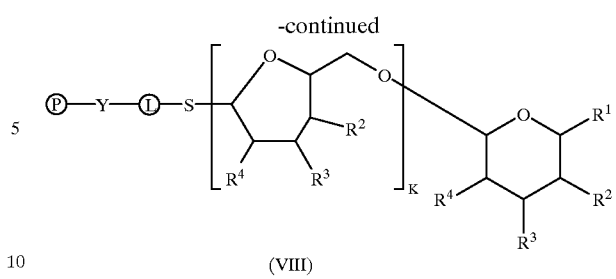

(VIII)

Deprotection preferably utilizes a transesterification with alcoholates such as NaOMe or a hydrolysis, for example with hydrazine in the presence of a solvent. Suitable solvents are aprotic, polar or nonpolar solvents or mixtures thereof. The reaction is carried out at from 0° C. to 120° C., preferably 0° C. to 60° C. The resulting compound VII is subsequently reacted with another sugar of the formula II as described above. The radicals $R^1$ to $R^4$ indicated in the formulae I and VII and II can be identical or different.

The reaction cycle can be carried out as often as desired, so that polysaccharides with high K values (K>10) can be synthesized. The polysaccharide can subsequently be eliminated from the solid phase as described with introduction of another substituent or with formation of a free hydroxyl group.

Compounds of the formula I are also suitable after elimination of at least one protective group for a further enzyme-catalyzed synthesis on carbohydrates and/or for assembling complex carbohydrates.

Thus, for example, proteases, lipases and/or esterases can be used, depending on the synthetic conditions, for forming ester or amide linkages or for cleaving a corresponding linkage. Glycosyltransferases or glycosidases can be used to attach further sugar residues to the thioglycoside. Combination of chemical and enzymatic synthesis is possible.

Protective groups suitable for the process according to the invention are in principle all those known from sugar synthesis, such as acetyl, benzoyl, pivaloyl, benzyl, 4-methoxybenzoyl, tert-butyldimethylsilyl, phenyl ditert-butyl, trimethylsilyl, benzylidene, 4-methoxybenzylidene, allyloxicarbonyl, propenyl, 4-pentenyl. Further protective groups which can be used for the process are described by Greene T. W. and Wats P. G. M. in Protective Groups in Organic Synthesis (John Wiley & Sons, Inc., 1991). Particular mention may be made of the following protective groups which are described therein for hydroxyl groups (page 10 et seq.), for carbonyl groups (page 175 et seq.), for carboxyl groups (page 224 et seq.), for amino groups (page 309 et seq.) and other protective groups which can be used (page 406 et seq.).

The process according to the invention can be carried out in a number of parallel automated synthetic batches. Mixtures of reactants can also be employed in one synthetic batch or parallel synthetic batches.

The process according to the invention is very suitable for generating a large number of structurally diverse compounds of the formulae I and V because the substituents $R^1$ to $R^{13}$ can be varied widely in a simple manner independently of one another.

Reactions on a polymeric support have great advantages by comparison with reactions in solution. Thus, considerably fewer impurities are found in the products, so that chromatographic fractionation is unnecessary. The good yields, the high purity of the eliminated products and the simple reaction procedure in the process according to the invention make its use very attractive for combinatorial synthesis. A particular advantage of this process is, for example, the fact that costly polymers do not need to be used because a low-cost crosslinker can be attached to any suitable solid phases for functionalization.

The process is also particularly suitable for preparing defined mixtures of carbohydrate derivatives of the formula I. This is done not by starting from a single substance which is bound to the solid phase, but by binding a mixture, preferably a mixture in which the stoichiometry and substances are known, to the solid phase.

The reactant bound to the solid phase is then reacted with the other reactants by the process described.

The advantage of this solid-phase synthesis is that a large number of individual compounds is rapidly generated, and they can subsequently be investigated for their activity in test systems. This large number of individual compounds form what are called substance libraries.

For testing, the substance mixtures can be employed either after fractionation or directly in the form of the mixtures. In the second case, a potential active substance is identified after the testing.

The invention furthermore relates to the use of the process according to the invention for preparing bound or free carbohydrate derivatives of the formulae I or V for generating substance libraries.

By this is meant both the generation, described above, of carbohydrate mixtures and the preparation of a large number of single substances of the formulae I or V, for example by carrying out many similar reactions in parallel, changing one reactant in each case.

Carrying out many similar reactions in parallel permits systematic variation of all the functional groups in the formulae I or V in a rapid manner.

The substance libraries which can be generated in this way can be quickly checked for a particular activity in mass screening. This greatly speeds up the search for potent active substances.

The invention furthermore relates to carbohydrate derivatives of the general formula I which are bound to a support. These compounds can be prepared by carrying out the abovementioned preparation process without eliminating the resulting carbohydrates of the formula I from the solid phase.

This means that the carbohydrate derivatives remain bound to the solid phase and can easily be employed as such in test methods, preferably in in vitro test systems.

The advantage of carbohydrate derivatives bound to the support is that they can be handled easily. For example, they can easily be isolated from the reaction solution by filtration or centrifugation.

EXAMPLES

In addition, identification of an active substance is considerably facilitated because the carbohydrate derivatives which are bound to a support are already isolated and thus separation is unnecessary.

The following examples serve to illustrate the invention further without restricting it in any way.

Example 1

1. Synthesis of the Glycosyl Donor 1,6-Di-O-acetyl-2,3,4-tri-O-benzyl-α,β-D-glucopyranoside (1)

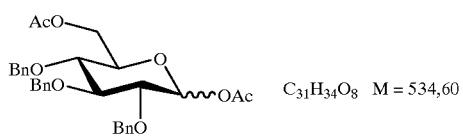

Compound 1 was prepared by a literature method of C. Schuerch et al. [(Carbohydr. Res. 73 (1979), 273–276)].

6-O-Acetyl-2,3,4-tri-O-benzyl-α,β-D-glucopyranose (2)

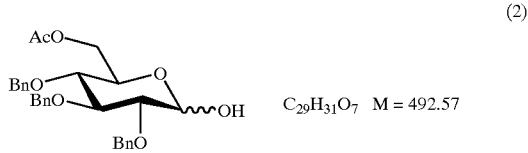

5 g (9.35 mmol) of compound 1 are dissolved in 20 ml of dimethylformamide. 0.95 g of hydrazinium acetate (10.28 mmol) is added and the mixture is heated at 50° C. for 20 min. The hydrazinium acetate dissolves completely, and a check by thin-layer chromatography (PE=petrolether/EA= ethyl acetate 2:1) shows that reaction is complete. The reaction solution is added to 20 ml of water and extracted three times with 50 ml of diethyl ether each time. The combined organic phases are dried over magnesium sulfate and concentrated under reduced pressure at a bath temperature of 50° C. The starting product (4.33 g, 94%) can be reacted without further purification. The physical data agree with those in the literature (Carbohydr. Res. 191 (1) (1989) 21–28).

O-6-O-Acetyl-2,3,4-tri-O-benzyl-D-glucopyranosyl) trichloroacetimidate (3)

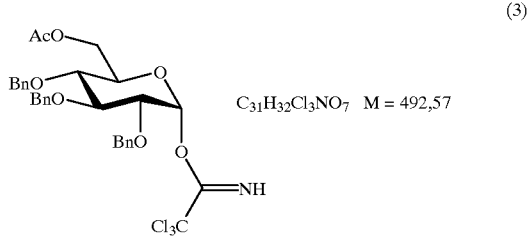

Compound 2 (4.3 g, 8.7 mmol) is dissolved together with 3.5 ml (34 mmol) of trichloroacetonitrile in 20 ml of dichloromethane at 23° C. Then 0.1 ml of 1,8-diazabicyclo [5.4.0]undec-7-ene is added. After 30 min, the thin-layer chromatogram (PE/EA 4:1) shows that reaction is complete. The reaction solution is concentrated under reduced pressure and filtered through a short silica gel column with PE/BE 2:1, adding 1% triethylamine to the eluent. 4.88 g (7.65 mmol, 88%) of product were obtained.

$^1$H-NMR (250 MHz): δ 2.0 (s, 3 H, OAc), 3.60 (dd, $^3J_{2,3}$=9.5 Hz, $^3J_{3,4}$=9.5 Hz, 1 H, 3-H), 3.74 (dd, $^3J_{1,2}$=3.5 Hz, $^3J_{2,3}$=9.5 Hz, 1 H, 2-H), 4.05 (m, 1 H, 5-H), 4.07 (d, $^3J_{3,4}$=9.5 Hz, $^3J_{4,5}$=9.5 Hz, 1 H, 4-H), 4.15–4.35 (m, 2 H, 2 6-H), 4.55–5.10 (m, 6 H, CH$_2$Ph), 6.46 (d, $^3J_{1,3}$=3.5 Hz, 1 H, 1-H), 7.15–7.45 (m, 6 H, phenyl, 8.61 (s, 1 H, NH).

Example 2

2. Functionalization of the Synthesis Polymer a) Without Protective Group

Divinylbenzene/polystyrene copolymer functionalized with 1,3-propanedithiol (4)

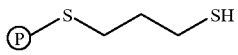

(4)

1 g of chloromethylated 1% divinylbenzene/polystyrene copolymer from Fluka is swollen in 10 ml of toluene. 1 ml of 1,3-propanedithiol (10 mmol) is added and mixed by swirling. After 15 min, 0.45 ml (3 mmol) of 1,8-diazabicyclo [5.4.0]undec-7-ene is added dropwise, and the reaction is left to stand at 23° C., swirling occasionally, for 24 h. The resin is filtered off and washed several times alternately with dichloromethane and dimthyforamie. It is then dried at 90° C. under reduced pressure for 12 h. The functionalization is determined by elemental analysis to be 0.5 mmol/g.

b) With Protective Group

1-Dimethoxytritylthio-3-propanol (5)

(5)

6.77 g of dimethoxytriphenylmethyl chloride (20 mmol) are dissolved in 40 ml of pyridine. At 10° C., 2 ml (18 mmol) of methyl 3-mercaptopropionate are added and the mixture is stirred at 23° C. for 14 h. The reaction solution is then diluted with 150 ml of diethyl ether and extracted with 20 ml of water. The organic phase is dried with magnesium sulfate and then concentrated under reduced pressure and coevaporated with toluene several times. The resulting crude product is dissolved in 40 ml of DMF. At 0° C., 820 mg of lithium aluminum hydride (21.6 mmol) are added in portions. The reaction is complete after 2 h (toluene/EA 5:1). Workup involves dilution with 10 ml of ethyl acetate, after 15 min with 100 ml of diethyl ether and then slowly with 80 ml of water. After stirring for 1 h, filtration through kieselguhr is followed by several washes with diethyl ether. The organic phase is dried and then concentrated, and two crystallizations from PE/EA (1:1) result in 6.1 g of compound 5 (86%).

$^1$H-NMR (250 Mhz [sic], CDCl$_3$): δ=1.25 (bs, 1 H, OH), 1.64 (tt, $^3$J=6.65 Hz, 2 H, CH$_2$), 2.28 (t, $^3$J=7.2 Hz, 2 H, CH$_2$), 3.58 (dt, $^3$J$_{OH,CH}$=5.7 Hz, $^3$J$_{CH,CH}$=6.65 Hz, 2 H, CH$_2$) 3.79 (s, 6 H, OCH$_3$), 6.7–7.4 (m, 13 H, phenyl).

Divinylbenzene/polystyrene copolymer functionalized with Propan-3-ol-1-thiol (6)

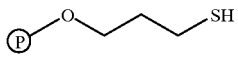

(6)

0.5 g of chloromethylated 1% divinylbenzene/polystyrene copolymer is swollen in 5 m.1 of tetrahydrofuran, and 632 mg (1.6 mmol) of 1-dimethoxytritylthio-3-propanol (5), 380 µl (1.92 mmol) of 15-crown-5 (=1,4,7,10,13-pentaoxacyclopentadecane) and 46 mg (1.92 mmol) of sodium hydride are added. After heating at 60° C. for 24 h, workup is carried out as described for compound 4. This is followed by washing with a 5% solution of trifluoroacetic acid in dichloromethane until the washings are colorless. The washing with dichloromethane and dimethylformamide is followed by drying at 90° C. for 12 h. Elemental analysis reveals a functionalization of 0.5 mmol/g.

Example 3

3. Method for Solid-phase Glycosylation

Glycosylated, fully protected synthesis polymer (7); n=1.5

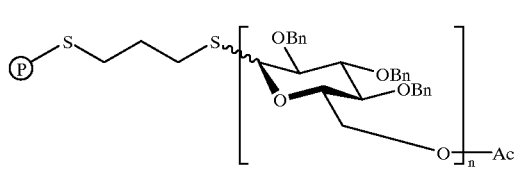

(7)

200 mg of the synthesis resin 4 are packed under protective gas into a glass cartridge (8×80 mm) which is then closed with Teflon stoppers. 191 mg (0.3 mmol) of compound 3 are dissolved in dichloromethane; this solution is injected into the reaction vessel and left to stand for 10 min swirling occasionally. Then 100 µl of a 0.5 M solution of trimethylsilyl triflate in dichloromethane are added and the reaction vessel is shaken horizontally for 1 h. It is subsequently washed alternately with dichloromethane and dichloromethane/acetonitrile 1:1 and dried under reduced pressure. The glycosylation reaction is checked for completeness by MALDI-TOF-MS. For this purpose, 2 mg of the resin 7 are treated with 0.1 ml of freshly prepared solution of dimethyl(methylthio)sulfonium tetrafluoroborate solution (DMTSB) in dichloromethane/methanol 9:1 (10 mg per ml) for 15 min. 10 µl of this suspension are then mixed with the same volume of a solution of 2,5-dihydroxybenzoic acid in acetonitrile. 0.8 µl of this mixture is taken and directly loaded onto the target of the mass spectrometer and, after drying for 5 min, measured.

Example 4

4. Method for Deacetylation on the Synthesis Resin

Glycosylated, 6-O-deacetylated synthesis resin (8); n=1–5

(8)

The glycosylated synthesis resin 7 (0.1 mmol) is mixed with 2 ml of dichloromethane and 0.2 ml of a 0.5 M solution of sodium methanolate in methanol. The reaction vessel is shaken for 2 h. Washing with dichloromethane is followed by shaking with a solution of two equivalents of 15-crown-5 in dichloromethane/methanol 20:1 for 20 min. Renewed washing with dichloromethane and with dichloromethane/acetonitrile 1:1 is followed by drying under reduced pressure. The reaction is checked as for synthesis resin 7.

Example 5

5. Elimination of the Oligosaccharides from the Glycosylated Synthesis Polymer 1-O-Methyl-α,β-D-glucopyranosyl-(1→6)-oligosaccharide (9); n=2–5

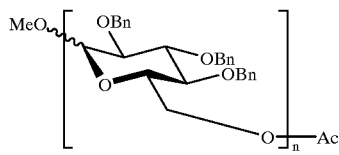
(9)

The glycosylated synthesis resin 7 (about 0.05 mmol, the weight varies with n) is swollen in 4 ml of dichloromethane/methanol 9:1, and 13 mg (0.1 mmol) of dimethyl (methylthio)sulfonium tetrafluoroborate and 13 μl of diisopropylethylamine (0.1 mmol) are added. After 2 h, the polymer is filtered off and washed with dichloromethane and dichloromethane/acetonitrile (1:1). The collected filtrates are diluted with 60 ml of diethyl ether and extracted twice with 15 ml of water. The dried organic phase is concentrated and purified on silica gel (toluene/EA 6:1).

The anomeric mixtures for n=2–5 are obtained in each case without contamination by sugars with longer or shorter chains detectable by mass spectroscopy. The α,β anomer ratio for each glycosylation step is ≈1.

$^1$H-NMR (600 Mhz [sic], CDCl$_3$): δ in ppm=4.95–5.02 H-1α, 4.25–4.30 H1-β. $^{13}$C-NMR (150.9 Mhz [sic], CDCl$_3$) δ: 97–99 C-1α, 104–106 C1-β.

General formula for compound 9: $C_{27n+3}H_{28n+6}O_{5n+2}$ M=432.515n+74.08

We claim:

1. A process for preparing carbohydrate derivatives of the formula I

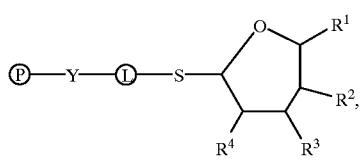
(I)

in which the variables and substituents have the following meanings:

(P) is a solid phase;
(L) is an aliphatic linker having 2 to 12 carbon atoms,
$R^1$ is $CHR^5R^6$, $R^5$,
$R^2$, $R^3$, $R^4$ independently of one another are hydrogen, XH, substituted or unsubstituted

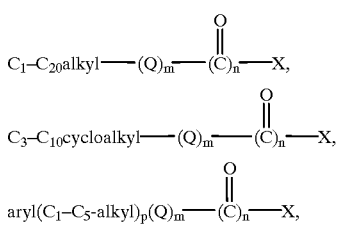

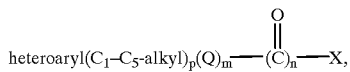

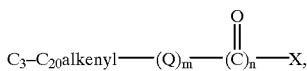

$(C_1-C_4\text{-alkyl})_3\text{SiO}$, diaryl$(C_1-C_5\text{-alkyl})\text{SiO}$, aryl $(C_1-C_5\text{-dialkyl})\text{SiO}$ or $R^7$ and m=0, 1; n=0, 1; p=0, 1;

or two adjacent radicals $R^2$, $R^3$, $R^4$, $R^6$ independently of one another form a substituted or unsubstituted arylalkylidene acetal or an alkylidene acetal, $R^5$ is hydrogen, substituted or unsubstituted $C_1-C_{20}$-alkyl, $C_3-C_{20}$-alkenyl, arylalkyl or aryl, $R^6$ is hydrogen, XH, substituted or unsubstituted

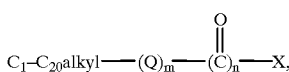
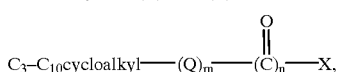
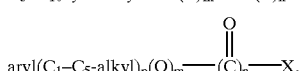
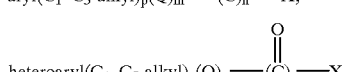
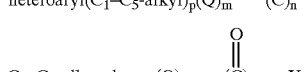

$(C_1-C_4\text{ alkyl})_3$ SiO, diaryl$(C_1-C_5\text{-alkyl})\text{SiO}$, aryl $(C_1-C_5\text{-dialkyl})\text{SiO}$ or $R^7$ and m=0, 1; n–0, 1; p=0, 1 or $(\text{aryl})_3\text{CO}$, $R^7$ is a group of the formula IV

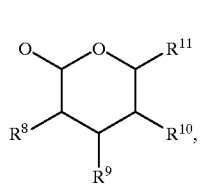
(IV)

where the substituents $R^8$, $R^9$, $R^{10}$, $R^{11}$ have the following meanings:

$R^8$, $R^9$, $R^{10}$ independently of one another have the meanings described for the radicals $R^2$, $R^3$, $R^4$ and may be identical to or different from the radicals $R^2$, $R^3$, $R^4$, $R^{11}$ is $CHR^5R^6$, $R^5$ or two adjacent radicals $R^8$, $R^9$, $R^{10}$, $R^6$ independently of one another may form a substituted or unsubstituted arylalkylidene acetal or an alkylidene acetal, Q is O, NH,
X is O, NR$^{12}$,
Y is O, S,
$R^{12}$ is hydrogen, substituted or unsubstituted $C_1-C_{10}$-alkyl, $C_3-C_8$-cycloalkyl, aryl, heteroaryl, arylalkyl, which comprises coupling compounds of the formula II

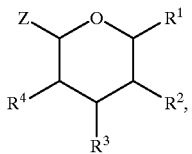
(II)

where Z is selected from the group $N^3$, halogen,

$OCH_2CH_2CH_2CH{=}CH_2$, $OPO_2H_2$, S-aryl, S-alkyl, in the presence of a promoter to a functionalized solid phase of the formula III

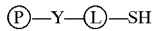
(III).

2. A process for preparing compounds of the formula I as claimed in claim 1, wherein a compound of the formula Ia

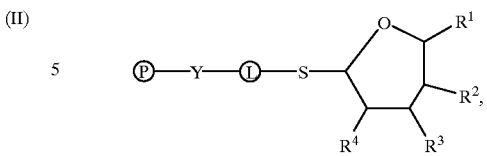
(Ia)

whose radicals $R^1$ to $R^{12}$ and whose variables (P), (L), Q, X, Y, n, m and p have the meanings stated for formula I in claim 1, with the proviso that at least one of the radicals $R^2$, $R^3$, $R^4$ or $R^6$ is XH, is reacted with a compound of the formula II in the presence of a promoter.

3. A process as claimed in claim 2, wherein compounds of the formula Ia are reacted with more than, exactly or less than one molar equivalent of the compounds of the formula II based on the XH groups in formula Ia.

4. The process of claim 2, wherein compounds of the formula Ia are reacted with one or more acylating, carbamoylating or alkylating reagents.

* * * * *